United States Patent [19]
Inouye et al.

[11] Patent Number: 5,093,240
[45] Date of Patent: Mar. 3, 1992

[54] VARIANT AEQUORIN GENES AND PROCESS FOR PRODUCING VARIANT AEQUORIN PROTEINS

[75] Inventors: Satoshi Inouye, Yokohamashi; Kouichi Kurose, Munakatashi; Yoshiyuki Sakaki, Fukuokashi, all of Japan

[73] Assignee: Chisso Corporation, Osaka, Japan

[21] Appl. No.: 105,602

[22] Filed: Oct. 8, 1987

[30] Foreign Application Priority Data

Oct. 15, 1986 [JP] Japan ................... 61-245108
Oct. 15, 1986 [JP] Japan ................... 61-245109
May 23, 1987 [JP] Japan ................... 62-126373
May 23, 1987 [JP] Japan ................... 62-126374

[51] Int. Cl.$^5$ .............. C12P 21/02; C12P 19/34; C12N 15/00; C12N 7/00; C12N 1/20; C07H 15/12; B07K 3/00
[52] U.S. Cl. .................... 435/69.1; 435/91; 435/172.3; 435/235.1; 435/252.3; 435/320.1; 435/252.33; 536/21; 530/350
[58] Field of Search ............ 435/68, 70, 91, 172.1, 435/172.3, 252.33, 320, 69.1, 71.2, 252.3; 536/27; 530/350; 935/16, 29, 41, 56, 60, 73

[56] References Cited
PUBLICATIONS

Shimomura et al., Nature, vol. 256, pp. 236-238 (1975).
Tsuji, F. I., Proc. Natl. Acad. Sci. U.S.A., vol. 83, pp. 8107-8111 (1986).
Inouye et al., Proc. Natl. Acad. Sci. U.S.A., vol. 82, pp. 3154-3158 (1985).
Charbonneau et al., Biochem., vol. 24, pp. 6762-6771 (1985).
Itakura et al., Science, vol. 209, pp. 1401-1405 (1980).

*Primary Examiner*—Richard A. Schwartz
*Assistant Examiner*—Joan Ellis
*Attorney, Agent, or Firm*—Wenderoth, Lind & Ponack

[57] ABSTRACT

Various variants of photoprotein aequorin (pAQ440), useful for elucidating the mechanism of its luminescence and thereby extending the possibility of concrete applications of aequorin protein, and a process for producing variant aequorin proteins are provided, which variants are obtained by converting base(s) in a specified order of the base arrangement of aequorin gene into other base(s), or by deleting a certain bases in specified continued orders thereof, according to site-specific mutagenesis method.

4 Claims, 1 Drawing Sheet

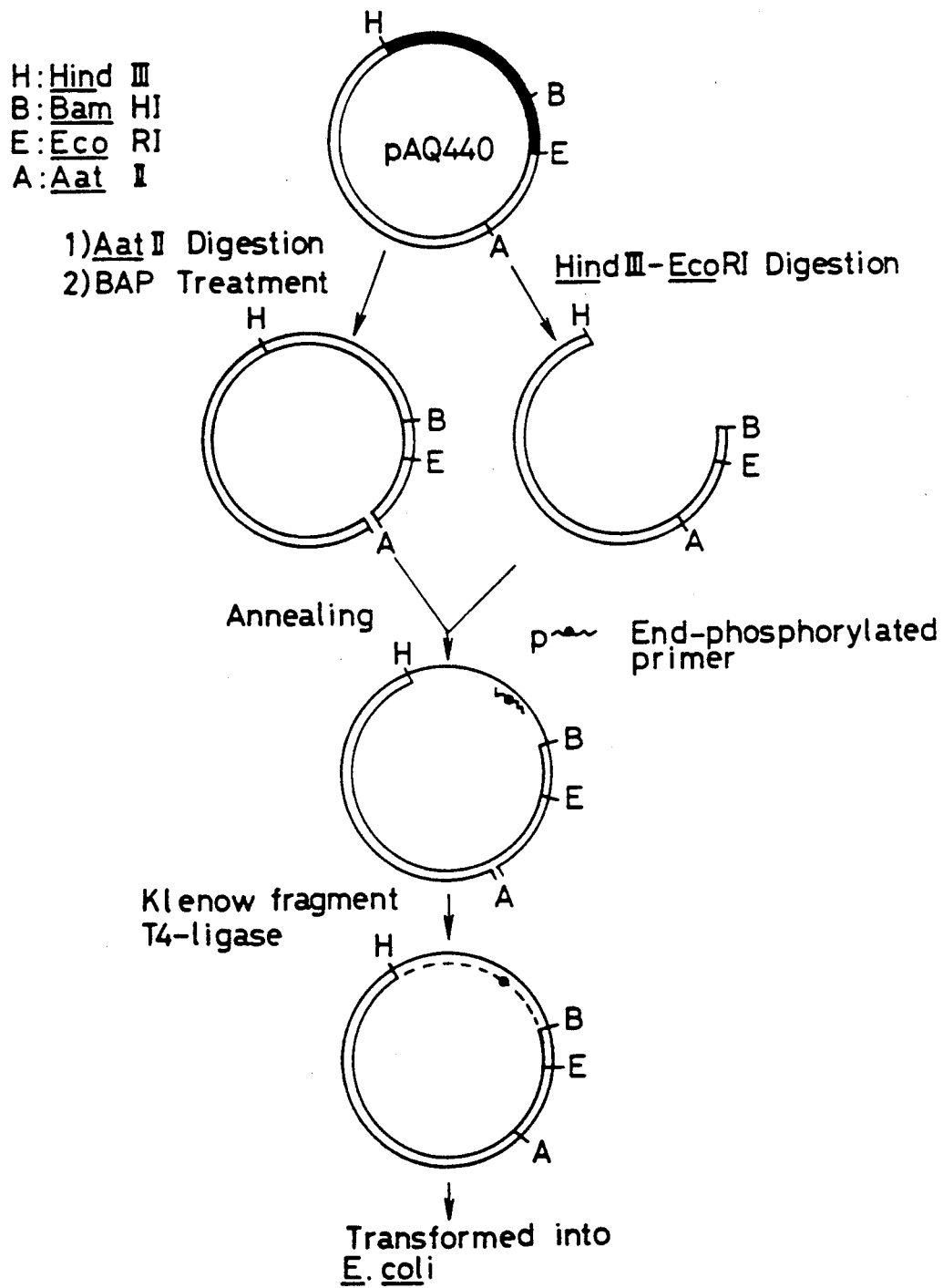

VARIANT AEQUORIN GENES AND PROCESS FOR PRODUCING VARIANT AEQUORIN PROTEINS

BACKGROUND OF THE INVENTION

1. Field of the Invention

This invention relates to variant aequorin genes and a process for producing variant aequorin proteins. More particularly it relates to variant aequorin genes prepared according to a site-specific mutagenesis method using a synthetic oligonucleotide, and a process for producing the above-mentioned proteins by the use of the above-mentioned genes.

2. Description of the Related Art

Aequorin existent in nature is the so-called photoprotein separated from photogenic Aequorea living in the sea, followed by separation and purification, and has been known as a biologically active substance in living body having a high utility value. Namely, since aequorin emits light by way of metal ions such as $Ca^{2+}$, $Sr^{2+}$, etc., it is utilized as a reagent for detecting trace $Ca^{2+}(10^{-9}M)$, and in particular, it has been confirmed to be effective for measuring intercellular $Ca^{2+}$. However, its production quantity is extremely small so that it is the present status that the quantity is insufficient even as an agent for research.

Thus, firstly the present inventors separated cDNA gene from photogenic Aequorea, identified it and referred to it as pAQ440 (Japanese patent application laid-open No. Sho 61-135586/1986). Further, we succeeded in producing aequorin protein inside Escherichia coli by means of recombinant DNA technique (Japanese patent application No. Sho 60-280259/1985), and also disclosed that it is possible to detect metal ions such as $Ca^{2+}$ by making use of this aequorin protein (Japanese patent application No. Sho 61-103849/1986).

However, as to its photogenic mechanism, many unclarified points are still present. Elucidation of the photogenic mechanism of aequorin protein and its correct understanding will extend a possibility of concrete applications of aequorin protein. More particularly, understanding of aequorin as a functional protein having a utility in the aspect of structure and function of protein will be linked to elucidation of the photogenic mechanism of aequorin and also will have a profound meaning in the aspect of protein engineering and further a commercial utilization value.

In view of the technical situation relative to aequorin protein, the present inventors have prepared variants of natural type aequorin gene (pAQ440) by means of recombinant DNA technique, and have succeeded in producing variant aequorin genes inside Escherichia coli by making use of the above genes. Further, by comparing the structure and function of these variant aequorin genes with those of pAQ440, it has become possible to more profoundly analyze the photogenic mechanism of the latter pAQ440.

As apparent from the foregoing, the object of the present invention is to provide many kinds of specified variant aequorin genes useful for making the above-mentioned analysis possible, and a process for producing variant aequorin proteins by the use of the above variant aequorin genes.

Further, as described above, as to the photogenic mechanism, the present inventors have analyzed the structure and function of the aequorin gene according to the site-specific mutagenesis method (Japanese patent application Nos. Sho 61-245108/1986 and Sho 61-245109/1986).

However, during the regeneration process of aequorin wherein aequorin which is light-emissive due to calcium is reconstructed in the presence of apoaequorin, coelenterazine as a substrate, molecular form oxygen and 2-mercaptoethanol as a reducing agent, it has been known that 2-mercaptoethanol is necessary to be in a high concentration. The reason why 2-mercaptoethanol is required is unclear, but a possibility of converting the —S—S—bond of aequorin protein(apoaequorin) into —SH,HS— is suggested.

Thus, it is very meaningful to produce variant aequorin proteins which do not require the presence of 2-mercaptoethanol as a reducing agent at the time of regeneration of aequorin by means of recombinant DNA technique, and this will be linked to elucidation of the regeneration mechanism of aequorin and further it will have a profound meaning in the aspect of protein engineering and also a utilization value in the scientific and commercial aspect.

In view of the above-mentioned technical situation of aequorin protein, the present inventors have prepared variants of natural type aequorin gene (pAQ440) by means of recombinant DNA technique, and have succeeded in producing variant aequorin genes inside Escherichia coli by making use of these genes.

Further, it has become possible to produce apoaequorin from which regeneration of aequorin is possible without needing the presence of 2-mercaptoethanol, using variant aequorin genes of the present invention as described later. The variant aequorin genes could have been obtained by converting G of TGC as a base arrangement which can form cysteine residual group on the aequorin gene, into C, to thereby exchange the serine residual group into the cysteine residual group in apoaequorin molecule.

SUMMARY OF THE INVENTION

The present invention resides in the following constitutions (1) to (4):

(1) In the following base arrangement of pAQ440 as aequorin gene:

GGGGGGGGGGGGGGGGGGGGGGGGGGGGGGG

60
GGGAATGCAATTCATCTTTGCATCAAAGAA
TTACATCAAATCTCTAGTTGATCAACTAAA

120
TTGTCTCGACAACAACAAGCAAACATGACA
AGCAAACAATACTCAGTCAAGCTTACATCA

180
GACTTCGACAACCCAAGATGGATTGGACGA
CACAAGCATATGTTCAATTTCCTTGATGTC

240
AACCACAATGGAAAAATCTCTCTTGACGAG
ATGGTCTACAAGGCATCTGATATTGTCATC

300
AATAACCTTGGAGCAACACCTGAGCAAGCC
AAACGACACAAAGATGCTGTAGAAGCCTTC

360
TTCGGAGGAGCTGGAATGAAATATGGTGTG
GAAACTGATTGGCCTGCATATATTGAAGGA

420
TGGAAAAAATTGGCTACTGATGAATTGGAG

-continued
AAATACGCCAAAAACGAACCAACGCTCATC

480
CGTATATGGGGTGATGCTTTGTTTGATATC
GTTGACAAAGATCAAAATGGAGCCATTACA

540
CTGGATGAATGGAAAGCATACACCAAAGCT
GCTGGTATCATCCAATCATCAGAAGATTGC

600
GAGGAAACATTCAGAGTGTGCGATATTGAT
GAAAGTGGACAACTCGATGTTGATGAGATG

660
ACAAGACAACATTTAGGATTTTGGTACACC
ATGGATCCTGCTTGCGAAAAGCTCTACGGT

720
GGAGCTGTCCCCTAAGAAGCTCTACGGTGG
TGATGCACCCTAGGAAGATGATGTGATTTT

780
GAATAAAACACTGATGAATTCAATCAAAAT
TTTCCAAATTTTTGAACGATTTCAATCGTT

840
TGTGTTGATTTTTGTAATTAGGAACAGATT
AAATCGAATGATTAGTTGTTTTTTTAATCA

900
ACAGAACTTACAAATCGAAAAAGTAAAAAA
AAAAAAAAAAAAAAAAAAAAAAAAAAAAAA

960
AAAAAAAAAAAAAAAAAAAAAAAAAAAA , variants having converted a base or bases indicated in the following items (i) to (xiii) into other definite base or bases, or having deleted bases indicated therein:
(i) a variant having converted the 220th base G into C;
(ii) a variant having converted the 238th base G into A;
(iii) a variant having converted the 307th base C into T, and also the 308th base A into T;
(iv) a variant having converted the 499th base G into C;
(v) a variant having converted the 568th base T into C;
(vi) a variant having converted the 569th base G into C;
(vii) a variant having converted the 590th base G into C;
(viii) a variant having converted the 607th base G into C;
(ix) a variant having converted the 625th base G into A;
(x) a variant having converted the 616th base G into C, and also the 625th base G into A;
(xi) a variant having converted the 674th base G into C;
(xii) a variant having deleted the 205th to the 207th bases GAT; and
(xiii) a variant having deleted the 592nd to the 594th bases GAT.
(2) In the following base arrangement of pAQ440 as aequorin gene:

GGGGGGGGGGGGGGGGGGGGGGGGGGGGGG

60
GGGAATGCAATTCATCTTTGCATCAAAGAA
TTACATCAAATCTCTAGTTGATCAACTAAA

-continued

120
TTGTCTCGACAACAACAAGCAAACATGACA
AGCAAACAATACTCAGTCAAGCTTACATCA

180
GACTTCGACAACCCAAGATGGATTGGACGA
CACAAGCATATGTTCAATTTCCTTGATGTC

240
AACCACAATGGAAAAATCTCTCTTGACGAG
ATGGTCTACAAGGCATCTGATATTGTCATC

300
AATAACCTTGGAGCAACACCTGAGCAAGCC
AAACGACACAAAGATGCTGTAGAAGCCTTC

360
TTCGGAGGAGCTGGAATGAAATATGGTGTG
GAAACTGATTGGCCTGCATATATTGAAGGA

420
TGGAAAAAATTGGCTACTGATGAATTGGAG
AAATACGCCAAAAACGAACCAACGCTCATC

480
CGTATATGGGGTGATGCTTTGTTTGATATC
GTTGACAAAGATCAAAATGGAGCCATTACA

540
CTGGATGAATGGAAAGCATACACCAAAGCT
GCTGGTATCATCCAATCATCAGAAGATTGC

600
GAGGAAACATTCAGAGTGTGCGATATTGAT
GAAAGTGGACAACTCGATGTTGATGAGATG

660
ACAAGACAACATTTAGGATTTTGGTACACC
ATGGATCCTGCTTGCGAAAAGCTCTACGGT

720
GGAGCTGTCCCCTAAGAAGCTCTACGGTGG
TGATGCACCCTAGGAAGATGATGTGATTTT

780
GAATAAAACACTGATGAATTCAATCAAAAT
TTTCCAAATTTTTGAACGATTTCAATCGTT

840
TGTGTTGATTTTTGTAATTAGGAACAGATT
AAATCGAATGATTAGTTGTTTTTTTAATCA

900
ACAGAACTTACAAATCGAAAAAGTAAAAAA
AAAAAAAAAAAAAAAAAAAAAAAAAAAAAA

960
AAAAAAAAAAAAAAAAAAAAAAAAAAAA , a process for producing a variant aequorin protein which comprises using
variants having converted a base or bases indicated in the following items (i) to (xiii) into other definite base or bases, or having deleted bases indicated therein:
(i) a variant having converted the 220th base G into C;
(ii) a variant having converted the 238th base G into A;
(iii) a variant having converted the 307th base C into T, and also the 308th base A into T;
(iv) a variant having converted the 499th base G into C;
(v) a variant having converted the 568th base T into C;
(vi) a variant having converted the 569th base G into C;

(vii) a variant having converted the 590th base G into C;
(viii) a variant having converted the 607th base G into C;
(ix) a variant having converted the 625th base G into A;
(x) a variant having converted the 616th base G into C, and also the 625th base G into A;
(xi) a variant having converted the 674th base G into C;
(xii) a variant having deleted the 205th to the 207th bases GAT; and
(xiii) a variant having deleted the 592nd to the 594th bases GAT.

(3) In the following base arrangement of pAQ440 as aequorin gene:

```
GGGGGGGGGGGGGGGGGGGGGGGGGGGGGG
                                          60
GGGAATGCAATTCATCTTTGCATCAAAGAA
TTACATCAAATCTCTAGTTGATCAACTAAA
                                         120
TTGTCTCGACAACAACAAGCAAACATGACA
AGCAAACAATACTCAGTCAAGCTTACATCA
                                         180
GACTTCGACAACCCAAGATGGATTGGACGA
CACAAGCATATGTTCAATTTCCTTGATGTC
                                         240
AACCACAATGGAAAAATCTCTCTTGACGAG
ATGGTCTACAAGGCATCTGATATTGTCATC
                                         300
AATAACCTTGGAGCAACACCTGAGCAAGCC
AAACGACACAAAGATGCTGTAGAAGCCTTC
                                         360
TTCGGAGGAGCTGGAATGAAATATGGTGTG
GAAACTGATTGGCCTGCATATATTGAAGGA
                                         420
TGGAAAAAATTGGCTACTGATGAATTGGAG
AAATACGCCAAAAACGAACCAACGCTCATC
                                         480
CGTATATGGGGTGATGCTTTGTTTGATATC
GTTGACAAAGATCAAAATGGAGCCATTACA
                                         540
CTGGATGAATGGAAAGCATACACCAAAGCT
GCTGGTATCATCCAATCATCAGAAGATTGC
                                         600
GAGGAAACATTCAGAGTGTGCGATATTGAT
GAAAGTGGACAACTCGATGTTGATGAGATG
                                         660
ACAAGACAACATTTAGGATTTTGGTACACC
ATGGATCCTGCTTGCGAAAAGCTCTACGGT
                                         720
GGAGCTGTCCCCTAAGAAGCTCTACGGTGG
TGATGCACCCTAGGAAGATGATGTGATTTT
                                         780
GAATAAAACACTGATGAATTCAATCAAAAT
TTTCCAAATTTTTGAACGATTTCAATCGTT
                                         840
TGTGTTGATTTTTGTAATTAGGAACAGATT
AAATCGAATGATTAGTTGTTTTTTTAATCA
                                         900
ACAGAACTTACAAATCGAAAAAGTAAAAAA
AAAAAAAAAAAAAAAAAAAAAAAAAAAAAA
```

-continued
```
                                         960
AAAAAAAAAAAAAAAAAAAAAAAAAAAAAA
``` variants having converted a base or bases indicated in the following items (i) to (iv) into other definite base or bases indicated therein:
(i) a variant having converted the 569th base G into C and the 590th base G into C;
(ii) a variant having converted the 590th G into C and the 674th G into C;
(iii) a variant having converted the 674th G into C and the 569th G into C; and
(iv) a variant having converted the 569th base G into C, the 590th base G into C and the 674th base G into C.

(4) In the following base arrangement of pAQ440 as aequorin gene:

```
GGGGGGGGGGGGGGGGGGGGGGGGGGGGGG
                                          60
GGGAATGCAATTCATCTTTGCATCAAAGAA
TTACATCAAATCTCTAGTTGATCAACTAAA
                                         120
TTGTCTCGACAACAACAAGCAAACATGACA
AGCAAACAATACTCAGTCAAGCTTACATCA
                                         180
GACTTCGACAACCCAAGATGGATTGGACGA
CACAAGCATATGTTCAATTTCCTTGATGTC
                                         240
AACCACAATGGAAAAATCTCTCTTGACGAG
ATGGTCTACAAGGCATCTGATATTGTCATC
                                         300
AATAACCTTGGAGCAACACCTGAGCAAGCC
AAACGACACAAAGATGCTGTAGAAGCCTTC
                                         360
TTCGGAGGAGCTGGAATGAAATATGGTGTG
GAAACTGATTGGCCTGCATATATTGAAGGA
                                         420
TGGAAAAAATTGGCTACTGATGAATTGGAG
AAATACGCCAAAAACGAACCAACGCTCATC
                                         480
CGTATATGGGGTGATGCTTTGTTTGATATC
GTTGACAAAGATCAAAATGGAGCCATTACA
                                         540
CTGGATGAATGGAAAGCATACACCAAAGCT
GCTGGTATCATCCAATCATCAGAAGATTGC
                                         600
GAGGAAACATTCAGAGTGTGCGATATTGAT
GAAAGTGGACAACTCGATGTTGATGAGATG
                                         660
ACAAGACAACATTTAGGATTTTGGTACACC
ATGGATCCTGCTTGCGAAAAGCTCTACGGT
                                         720
GGAGCTGTCCCCTAAGAAGCTCTACGGTGG
TGATGCACCCTAGGAAGATGATGTGATTTT
                                         780
GAATAAAACACTGATGAATTCAATCAAAAT
TTTCCAAATTTTTGAACGATTTCAATCGTT
                                         840
TGTGTTGATTTTTGTAATTAGGAACAGATT
AAATCGAATGATTAGTTGTTTTTTTAATCA
                                         900
ACAGAACTTACAAATCGAAAAAGTAAAAAA
```

-continued

AAAAAAAAAAAAAAAAAAAAAAAAAAAAAA

960

AAAAAAAAAAAAAAAAAAAAAAAAAAAA , a process for producing a variant aequorin protein which comprising using variants having converted a base or bases indicated in the following items (i) to (iv) into other definite base or bases indicated therein:

(i) a variant having converted the 569th base G into C and the 590th base G into C;

(ii) a variant having converted the 590th G into C and the 674th G into C;

(iii) a variant having converted the 674th G into C and the 569th G into C; and (iv) a variant having converted the 569th base G into C, the 590th base G into C and the 674th base G into C.

BRIEF DESCRIPTION OF THE DRAWING

The accompanying drawing shows a chart illustrating the site-specific mutagenesis method of Example 1 of the present invention.

DETAILED DESCRIPTION OF PREFERRED EMBODIMENTS

The variant genes of the present invention may be produced through the process as illustrated in the accompanying drawing. According to the process of the present invention, variations as mentioned later were introduced into the aequorin gene by the use of a synthetic oligonucleotide and according to a site-specific mutagenesis method. The variation process has no particular limitation, but for example, gap-duplex process (Morinaga et al, Bio/Technology, Vol. 2, 636-639 (1984) may be employed. According to the process, for example, a synthetic oligonucletide is used as a variation source as shown later in Table 1. Such a synthetic oligonucleotide may be synthesized employing a commercially available automatic DNA synthesis apparatus and its purification is preferably carried out employing a high performance liquid chromatography. The purified product is subjected to end-phosphorylation in a conventional manner to obtain a primer for preparing a plasmid.

On the other hand, an Eco RI-Hind III fragment and an Aat II fragment of a plasmid pAQ440 shown in the accompanying drawing are used and the Aat II fragment is subjected to dephosphorylation treatment in a conventional manner.

The two fragments based on pAQ440, obtained as above, together with the above-mentioned end-phosphorylated primer are, for example, subjected to three-stage treatment (treatment at definite temperatures and for definite times) to carry out annealing. The three stages refer to a combination consisting of an order of e.g. (100° C., 5 minutes), (30° C., 30 minutes) and (4° C., 30 minutes).

Next, with the resulting variant pAQ gene, transformation into E. coli is carried out as follows:

For example, dXTP (X=G.A.T.C.) obtained as above and Klenow fragment (E. coli polymerase) are reacted in the presence of T4-ligase to prepare a duplex chain. The thus formed plasmid duplex chain is transformed into E. coli in a conventional manner. Further, the variant plasmid (variant of pAQ440) is screened using the above-mentioned respective variant source primers as probes, according to colony hybridization. The identification method of the variant has no particular limitation, but the base arrangement is determined e.g. according to dideoxy method (Hattori et al, Anal. Biochem. 152, 232-238, 1986) to detect the variant base.

Next, in the present invention (the invention of production process), production of aequorin protein inside Escherichia coli is carried out using the above-mentioned variant aequorin gene.

Namely, the outline of the production is as follows:

the cDNA fragment of Hind III-Eco RI of the variant pAQ440 gene is subjected to cloning into the Hind III-Eco RI part of the plasmid pUC9-2 having a promoter of lac; the resulting plasmid is transformed into Escherichia coli such as HB101 (D1210i$^Q$) strain; and using the resulting Escherichia coli and an expression derivative such as IPTG, an aequorin protein is produced inside Escherichia coli.

The production process and the bacterial bodies-collecting process are carried out in a conventional manner. The collected bacterial bodies are dissolved in a suitable known buffer solution, followed by breaking the bacterial bodies in a conventional manner such as ultrasonic wave treatment and obtaining the supernatant by means of centrifugal treatment to use it as an enzymatic solution for measurement.

The method for measuring the luminescence relative to this solution is carried out as follows:

With a definite quantity of the solution are mixed a substrate (coelenterazine) and a reducing agent (2-mercaptoethanol) each in a definite quantity in the case of the above-mentioned inventions (1) and (2), while with the definite quantity of the solution is not mixed 2-mercaptomethanol in the case of the above-mentioned inventions (3) and (4), followed by maturing the resulting respective solutions under ice-cooling for 2 or 3 hours, transferring the resulting solutions into a reaction cell inside a phototube measurement apparatus, further injecting a definite quantity of $CaCl_2$ solution into the cell and measuring the resulting luminescence.

The synthetic oligonucleotide (primer) of the above inventions (1) and (2) is shown later in Table 1 of Example 1, and the aequorin activity of the primer is shown later in Table 2. The extent to which the aequorin activity varies or is extinct depending on what a site the base arrangement of aequorin gene is varied or base(s) therein are removed at is apparent from Tables 1 and 2.

The synthetic oligonucleotide (primer) to be measured, of the above-inventions (3) and (4) is shown later in Table 3 of Example 2, and the aequorin activity of the primer is shown later in Table 4 of the Example. It is apparent from Tables 3 and 4 that aequorin is reproduced by varying the base arrangement of aequorin gene, even when no 2-mercaptoethanol is added.

In particular, in the case of Cl+2+3S wherein the cysteine residual groups at all of the three parts have been converted into serine residual groups, it is apparent that aequorin is reproduced almost completely.

The present invention will be described in more detail by way of Examples.

EXAMPLE 1

1) Introduction of mutagenesis into aequorin gene (pAQ440) according to a site-specific mutagenesis process using a synthetic oligonucleotide (see the accompanying drawing)

The site-specific mutagenesis process was carried out according to gap-duplex process of Morinaga et al (Bio/Technology, Vol. 2, 630–639 (1984)). Namely, as shown later in Table 1, a synthetic oligonucleotide was used as a variation source. As the synthetic oligonucleotide, there was used a product obtained by preparing a raw product by means of an automatic DNA synthesis apparatus manufactured by ABI Company, followed by purifying it according to high performance liquid chromatography and carrying out end-phosphorylation with T4 kinase. Eco RI-Hind III fragment and Aat II fragment of pAQ440 were used, and Aat II fragment was treated with an alkali phosphatase to carry out dephosphorylation. These two fragments together with the primer were treated at 100° C. for 5 minutes, followed by allowing the resulting material to stand at 30° C. for 3 minutes and further at 4° C. for 30 minutes to carry out annealing and reacting dXTP (X=G, A, T, C) with Klenow fragment (Escherichia coli polymerase) in the presence of T4-ligase to prepare a duplex chain.

The thus formed plasmid duplex chain was transformed into E. coli in a conventional manner, and the variant plasmid (variant of pAQ440) was screened by colony hybridization, using the respective variant source primers as probes. As to the ascertainment of the variant, the base arrangement was determined according to the dideoxy process of Hattori et al (Anal. Biochem. 152, 232–238, 1986) and the variant base was detected.

2) Production of variant aequorin protein inside E. coli by the use of various variant aequorin genes cDNA fragment of Hind III-Eco RI of variant pAQ440 gene was subjected to cloning into the Hind III-Eco RI part of plasmid pUC9-2 having lac promoter, and transforming into E. coli HB101 (D1210i$^Q$) strain to produce variant aequorin protein inside E. coli by means of expression inducer IPTG.

Namely, $1/100$ of the quantity of the bacterial bodies obtained by cultivating pUC9-2 plasmid containing the variant aequorin gene for 12 hours was added to a L-broth medium (10 ml) containing Ampicillin (50 μg/ml), followed by cultivating the mixture at 37° C. for 2 hours, adding IPTG so as to give a final concentration of 1 mM, further cultivating the mixture at 37° C. for 2 hours, collecting the resulting bacterial bodies, washing them with M9 salt solution (5 ml), dissolving the resulting washed material in 20 mM Tris-HCl buffer (pH 7.6) (2.5 ml) containing 10 mM EDTA, breaking the bacterial bodies by supersonic wave treatment (60 seconds), carrying out centrifugal separation at 10,000 rpm for 10 minutes and using the resulting supernatant as an enzyme solution to be measured.

As to the measurement method, coelenterazine as a substrate (6 μg) and 2-mercaptoethanol (10 μl) were added to the enzyme solution (1 ml), followed by allowing the mixture to stand on ice for 2 to 3 hours, transferring it into a reaction cell in a phototube measurement apparatus, further pouring 20 mM $CaCl_2$ (1.5 ml) therein and measuring the resulting luminescence. The results are shown in Table 2.

TABLE 1

Synthetic oligonucleotide (primer) used in the site-specific mutagenesis method and the variation site

| Variation site | Name of primer | Synthetic oligonucleotides 5'                 3' |
|---|---|---|
| 220th | G1R | ACCACAATCGAAAAATC = |
| 449th | G2R | ATCAAAATCGAGCCATT = |
| 607th | G3R | TGAAAGTCGACAACTCG = |
| 569th | C1S | CAGAAGATTCCGAGGAA = |
| 568th | C1R | CAGAAGATCGCGAGGAA = |
| 590th | C2S | CAGAGTGTCCGATATTG = |
| 674th | C3S | TCCTGCTTCCGAAAAGC = |
| 307 & 308th | HF | CCAAACGATTCAAAGAT == |
| 238th | E35K | TCTTGACAAGATGGTCT = |
| 625th | E164K | TGTTGATGAGATGACAA = |
| 616 & 625th | D161H+K | AACTCGATGTTGATAAG4ATG = = |
| 205–207th | 24ΔD | CAATTTCCTT ... GTCAACCACA |
| 592–515th | 153ΔD | CAGAGTGTGC ... ATTGATGAAA |

=; Variation site
.; Deleted site

TABLE 2

Production of variant aequorin inside Escherichia coli

|  | Activity ×10$^{-8}$ Quanta/sec. |
|---|---|
| (Measurement 1) |  |
| Control (Aequorin) | 38.9 |
| G1R | 0 |
| G2R | 19.2 |
| G3R | 37.9 |
| HF | 0 |
| E35K | 0 |
| E164K | 0 |
| D161H + K | 0 |
| 24ΔD | 0 |
| 153ΔD | 0 |
| (Measurement 2) |  |
| Control (Aequorin) | 22.9 |
| C1S | 15.4 |
| C1R | 11.0 |
| C2S | 13.6 |
| C3S | 6.8 |

EXAMPLE 2

Example 1 was repeated except that the synthetic oligonucleotide (primer) used in the site-specific mutagenesis method and the variation site were varied. The variant sources used are shown in Table 3 and the results are shown in Table 4.

TABLE 3

Synthetic oligonucleotide (primer) used in the site-specific mutagenesis method and the variation site

| Variation site | Name of primer | Primer base arrangement 5'                 3' |
|---|---|---|
| 569th | C1S | CAGAAGATTCCGAGGAA = |
| 590th | C2S | CAGAGTGTCCGATATTG = |

TABLE 3-continued

Synthetic oligonucleotide (primer) used in the site-specific mutagenesis method and the variation site

| Variation site | Name of primer | Primer base arrangement 5' 3' |
|---|---|---|
| 674th | C3S | TCCTGCTTCCGAAAAGC |

TABLE 4

Reproduction of variant aequorins produced inside *Escherichia coli* (addition effect of 2-mercaptoethanol)

| | Relative activity value (%) 2-Mercaptoethanol | |
|---|---|---|
| Variant aequorin | Non-addition | Addition |
| Control (Aequorin) | 8 | 100 |
| C1S | 14 | 54 |
| C2S | 21 | 68 |
| C3S | 30 | 18 |
| C1 + 2S | 0 | 1 |
| C2 + 3S | 54 | 26 |
| C3 + 1S | 36 | 8 |
| C1 + 2 + 3S | 95 | 21 |

Note.
In the above table, 100% refers to 3.0 × 10$^{-9}$ light quantum/sec.
C1 + 2S: a variant obtained by converting the first and second cysteines into serines;
C2 + 3S: a variant obtained by converting the second and third cysteines into serines;
C3 + 1S: a variant obtained by converting the third and first cysteines into serines; and
C1 + 2 + 3S: a variant obtained by converting the first, second and third cysteines into serines.

What we claim is:

1. A DNA molecule encoding a variant aequorin photoprotein, said DNA molecule comprising a nucleotide sequence derived from the following nucleotide sequence of pAQ440 aequorin gene:

GGGGGGGGGGGGGGGGGGGGGGGGGGGGGG

60
GGGAATGCAATTCATCTTTGCATCAAAGAA
TTACATCAAATCTCTAGTTGATCAACTAAA

120
TTGTCTCGACAACAACAAGCAAACATGACA
AGCAAACAATACTCAGTCAAGCTTACATCA

180
GACTTCGACAACCCAAGATGGATTGGACGA
CACAAGCATATGTTCAATTTCCTTGATGTC

240
AACCACAATGGAAAAATCTCTCTTGACGAG
ATGGTCTACAAGGCATCTGATATTGTCATC

300
AATAACCTTGGAGCAACACCTGAGCAAGCC
AAACGACACAAAGATGCTGTAGAAGCCTTC

360
TTCGGAGGAGCTGGAATGAAATATGGTGTG
GAAACTGATTGGCCTGCATATATTGAAGGA

420
TGGAAAAAATTGGCTACTGATGAATTGGAG
AAATACGCCAAAAACGAACCAACGCTCATC

480
CGTATATGGGGTGATGCTTTGTTTGATATC
GTTGACAAAGATCAAAATGGAGCCATTACA

540
CTGGATGAATGGAAAGCATACACCAAAGCT
GCTGGTATCATCCAATCATCAGAAGATTGC

600
GAGGAAACATTCAGAGTGTGCGATATTGAT
GAAAGTGGACAACTCGATGTTGATGAGATG

660
ACAAGACAACATTTAGGATTTTGGTACACC
ATGGATCCTGCTTGCGAAAAGCTCTACGGT

720
GGAGCTGTCCCCTAAGAAGCTCTACGGTGG
TGATGCACCCTAGGAAGATGATGTGATTTT

780
GAATAAAACACTGATGAATTCAATCAAAAT
TTTCCAAATTTTTGAACGATTTCAATCGTT

840
TGTGTTGATTTTTGTAATTAGGAACAGATT
AAATCGAATGATTAGTTGTTTTTTTAATCA

900
ACAGAACTTACAAATCGAAAAAGTAAAAAA
AAAAAAAAAAAAAAAAAAAAAAAAAAAAAA

960
AAAAAAAAAAAAAAAAAAAAAAAAAAAA , wherein said derived nucleotide sequence varies from the nucleotide sequence of pAQ440 aequorin gene according to at least one member selected from the group consisting of the following:

(i) the 220th nucleotide is converted from G to C;
(ii) the 238th nucleotide is converted from G to A;
(iii) the 307th nucleotide is converted from C to T and the 308th nucleotide is converted from A to T;
(iv) the 499th nucleotide is converted from G to C;
(v) the 568th nucleotide is converted from T to C;
(vi) the 569th nucleotide is converted from G to C;
(vii) the 590th nucleotide is converted from G to C;
(viii) the 607th nucleotide is converted from G to C;
(ix) the 625th nucleotide is converted from G to A;
(x) the 616th nucleotide is converted from G to C and the 625th nucleotide is converted from G to A;
(xi) the 674th nucleotide is converted from G to C;
(xii) the 205th through the 207th nucleotides are deleted (GAT); and
(xiii) the 592th through the 594th nucleotides are deleted (GAT).

2. A process for producing a variant aequorin photoprotein, said process comprising the steps of preparing a DNA molecule encoding a variant aequorin photoprotein, said DNA molecule comprising a nucleotide sequence derived from the following nucleotide sequence of pAQ440 aequorin gene:

GGGGGGGGGGGGGGGGGGGGGGGGGGGGGG

60
GGGAATGCAATTCATCTTTGCATCAAAGAA
TTACATCAAATCTCTAGTTGATCAACTAAA

120
TTGTCTCGACAACAACAAGCAAACATGACA
AGCAAACAATACTCAGTCAAGCTTACATCA

180
GACTTCGACAACCCAAGATGGATTGGACGA
CACAAGCATATGTTCAATTTCCTTGATGTC

240
AACCACAATGGAAAAATCTCTCTTGACGAG
ATGGTCTACAAGGCATCTGATATTGTCATC

-continued

```
                              300
AAT AACCT T GGAGC AAC ACCT GAGC AAGCC
AAACGACACAAAGATGCT GT AGAAGCCT T C

360
TT CGGAGGAGCT GGAAT GAAAT AT GGT GT G
GAAACT GAT T GGCCT GCAT AT AT T GAAGGA

420
T GGAAAAAAT T GGCT ACT GAT GAAT T GGAG
AAATACGCC AAAAACGAACC AACGCT CAT C

480
CGT AT AT GGGGT GAT GCT T T GT T T GAT ATC
GT T GAC AAAGAT C AAAAT GGAGCC AT T ACA

540
CT GGAT GAAT GGAAAGC AT ACACC AAAGCT
GCT GGT AT C AT CCAAT CAT CAGAAGAT T GC

600
GAGGAAAC AT T CAGAGT GT GCGAT AT T GAT
GAAAGT GGAC AACT CGAT GT T GAT GAGATG

660
ACAAGAC AAC AT T T AGGAT T T T GGT ACACC
AT GGAT CCT GCT T GCGAAAAGCT CT ACGGT

720
GGAGCT GT CCCCT AAGAAGCT CT ACGGT GG
T GAT GCACCCT AGGAAGAT GAT GT GAT T TT

780
GAAT AAAACACT GAT GAAT T CAAT CAAAAT
TTT CCAAAT T T T T GAACGAT T T CAAT CGT T

840
T GT GT T GAT T T T T GT AAT T AGGAAC AGAT T
AAAT CGAAT GAT T AGT T GT T T T T T T AAT CA

900
ACAGAACT T ACAAAT CGAAAAAGT AAAAAA
AAAAAAAAAAAAAAAAAAAAAAAAAAAAAA

960
AAAAAAAAAAAAAAAAAAAAAAAAAAAAA   ,
``` wherein said derived nucleotide sequence varies from the nucleotide sequence of pAQ440 aequorin gene according to at least one member selected from the group consisting of the following:
  (i) the 220th nucleotide is converted from G to C;
  (ii) the 238th nucleotide is converted from G to A;
  (iii) the 307th nucleotide is converted from C to T and the 308th nucleotide is converted from A to T;
  (iv) the 499th nucleotide is converted from G to C;
  (v) the 568th nucleotide is converted from T to C;
  (vi) the 569th nucleotide is converted from G to C;
  (vii) the 590th nucleotide is converted from G to C;
  (viii) the 607th nucleotide is converted from G to C;
  (ix) the 625th nucleotide is converted from G to A;
  (x) the 616th nucleotide is converted from G to C and the 625th nucleotide is converted from G to A;
  (xi) the 674th nucleotide is converted from G to C;
  (xii) the 205the through the 207th nucleotides are deleted (GAT); and
  (xiii) the 592th through the 594th nucleotides are deleted (GAT),
transforming a bacterial cell with said DNA molecule, wherein the bacterial cell is capable of producing the variant aequorin photoprotein from said DNA molecule,
cultivating the bacterial cell, and
obtaining the variant aequorin photoprotein from the bacterial cell.

3. A DNA molecule encoding a variant aequorin photoprotein, said DNA molecule comprising a nucleotide sequence derived from the following nucleotide sequence of pAQ440 aequorin gene:

```
GGGGGGGGGGGGGGGGGGGGGGGGGGGGGG

60
GGGAAT GCAAT T CAT CT T T GCAT C AAAGAA
T T ACAT CAAAT CT CT AGT T GAT C AACT AAA

120
T T GT CT CGAC AAC AAC AAGC AAAC AT GACA
AGCAAACAAT ACT CAGT C AAGCT T ACAT CA

180
GACT T CGAC AACCC AAGAT GGAT T GGACGA
CACAAGC AT AT GT T CAAT T T CCT T GAT GT C

240
AACC ACAAT GGAAAAAT CT CT CT T GACGAG
AT GGT CT ACAAGGC AT CT GAT AT T GT CAT C

300
AAT AACCT T GGAGC AAC ACCT GAGC AAGCC
AAACGACACAAAGATGCT GT AGAAGCCT T C

360
TT CGGAGGAGCT GGAAT GAAAT AT GGT GT G
GAAACT GAT T GGCCT GCAT AT AT T GAAGGA

420
T GGAAAAAAT T GGCT ACT GAT GAAT T GGAG
AAATACGCC AAAAACGAACC AACGCT CAT C

480
CGT AT AT GGGGT GAT GCT T T GT T T GAT ATC
GT T GAC AAAGAT C AAAAT GGAGCC AT T ACA

540
CT GGAT GAAT GGAAAGC AT ACACC AAAGCT
GCT GGT AT C AT CCAAT CAT CAGAAGAT T GC

600
GAGGAAAC AT T CAGAGT GT GCGAT AT T GAT
GAAAGT GGAC AACT CGAT GT T GAT GAGATG

660
ACAAGAC AAC AT T T AGGAT T T T GGT ACACC
AT GGAT CCT GCT T GCGAAAAGCT CT ACGGT

720
GGAGCT GT CCCCT AAGAAGCT CT ACGGT GG
T GAT GCACCCT AGGAAGAT GAT GT GAT T TT

780
GAAT AAAACACT GAT GAAT T CAAT CAAAAT
TTT CCAAAT T T T T GAACGAT T T CAAT CGT T

840
T GT GT T GAT T T T T GT AAT T AGGAAC AGAT T
AAAT CGAAT GAT T AGT T GT T T T T T T AAT CA

900
ACAGAACT T ACAAAT CGAAAAAGT AAAAAA
AAAAAAAAAAAAAAAAAAAAAAAAAAAAAA

960
AAAAAAAAAAAAAAAAAAAAAAAAAAAAA   ,
``` wherein said derived nucleotide sequence varies from the nucleotide sequence of pAQ440 aequorin gene according to at least one member selected from the group consisting of the following:
  (i) the 569th nucleotide is converted from G to C and the 590th nucleotide is converted from G to C;
  (ii) the 590th nucleotide is converted from G to C and the 674th nucleotide is converted from G to C;
  (iii) the 674th nucleotide is converted from G to C and the 569th nucleotide is converted from G to C;

(iv) the 569th nucleotide is converted from G to C, the 590th nucleotide is converted from G to C, and the 674th nucleotide is converted from G to C.

4. A process for producing a variant aequorin photoprotein, said process comprising the steps of
preparing a DNA molecule encoding a variant aequorin photoprotein, said DNA molecule comprising a nucleotide sequence derived from the following nucleotide sequence of pAQ440 aequorin gene:

GGGGGGGGGGGGGGGGGGGGGGGGGGGGG

```
                                              60
GGGAATGCAATTCATCTTTGCATCAAAGAA
TTACATCAAATCTCTAGTTGATCAACTAAA

120
TTGTCTCGACAACAACAAGCAAACATGACA
AGCAAACAATACTCAGTCAAGCTTACATCA

180
GACTTCGACAACCCAAGATGGATTGGACGA
CACAAGCATATGTTCAATTTCCTTGATGTC

240
AACCACAATGGAAAAATCTCTCTTGACGAG
ATGGTCTACAAGGCATCTGATATTGTCATC

300
AATAACCTTGGAGCAACACCTGAGCAAGCC
AAACGACACAAAGATGCTGTAGAAGCCTTC

360
TTCGGAGGAGCTGGAATGAAATATGGTGTG
GAAACTGATTGGCCTGCATATATTGAAGGA

420
TGGAAAAAATTGGCTACTGATGAATTGGAG
AAATACGCCAAAAACGAACCAACGCTCATC

480
CGTATATGGGGTGATGCTTTGTTTGATATC
GTTGACAAAGATCAAAATGGAGCCATTACA

540
CTGGATGAATGGAAAGCATACACCAAAGCT
GCTGGTATCATCCAATCATCAGAAGATTGC

600
GAGGAAACATTCAGAGTGTGCGATATTGAT
GAAAGTGGACAACTCGATGTTGATGAGATG

660
ACAAGACAACATTTAGGATTTTGGTACACC
ATGGATCCTGCTTGCGAAAAGCTCTACGGT

720
GGAGCTGTCCCCTAAGAAGCTCTACGGTGG
TGATGCACCCTAGGAAGATGATGTGATTTT

780
GAATAAAACACTGATGAATTCAATCAAAAT
TTTCCAAATTTTTGAACGATTTCAATCGTT

840
TGTGTTGATTTTTGTAATTAGGAACAGATT
AAATCGAATGATTAGTTGTTTTTTTAATCA

900
ACAGAACTTACAAATCGAAAAAGTAAAAAA
AAAAAAAAAAAAAAAAAAAAAAAAAAAAAA

960
AAAAAAAAAAAAAAAAAAAAAAAAAAAA  ,
``` wherein said derived nucleotide sequence varies from the nucleotide sequence of pAQ440 aequorin gene according to at least one member selected from the group consisting of the following:
 (i) the 569th nucleotide is converted from G to C and the 590th nucleotide is converted from G to C;
 (ii) the 590th nucleotide is converted from G to C and the 674the nucleotide is converted from G to C;
 (iii) the 674th nucleotide is converted from G to C and the 569th nucleotide is converted from G to C;
 (iv) the 569th nucleotide is converted from G to C, the 590th nucleotide is converted from G to C, and the 674th nucleotide is converted from G to C,
transforming a bacterial cell with said DNA molecule, wherein the bacterial cell is capable of producing the variant aequorin photoprotein from said DNA molecule,
cultivating the bacterial cell, and
obtaining the variant aequorin photoprotein from the bacterial cell.

* * * * *